(12) United States Patent
Sharma

(10) Patent No.: US 10,176,694 B2
(45) Date of Patent: *Jan. 8, 2019

(54) AIRCRAFT OCCUPANT SEAT FOR AIRCRAFT OCCUPANT HEALTH, SAFETY, AND COMFORT MANAGEMENT

(71) Applicant: AIRBUS GROUP INDIA PRIVATE LIMITED, Bangalore (IN)

(72) Inventor: Anurag Sharma, Bangalore (IN)

(73) Assignee: AIRBUS GROUP INDIA PRIVATE LIMITED, Bangalore, Karnataka (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/245,217

(22) Filed: Aug. 24, 2016

(65) Prior Publication Data
US 2017/0069194 A1 Mar. 9, 2017

(30) Foreign Application Priority Data
Sep. 9, 2015 (IN) .......................... 4790/CHE/2015

(51) Int. Cl.
*G08B 21/04* (2006.01)
*B64D 45/00* (2006.01)
(Continued)

(52) U.S. Cl.
CPC ........ *G08B 21/0461* (2013.01); *A61B 5/0816* (2013.01); *A61B 5/6891* (2013.01); *A61M 21/02* (2013.01); *B64D 11/06* (2013.01); *B64D 11/062* (2014.12); *B64D 11/0626* (2014.12); *B64D 11/0646* (2014.12); *B64D 45/00* (2013.01); *G02B 6/02076* (2013.01); *A61B 2560/0242* (2013.01); *A61M 2021/0027* (2013.01); *A61M 2021/0044* (2013.01); *A61M 2021/0066* (2013.01); *A61M 2021/0083* (2013.01)

(58) Field of Classification Search
CPC .............. G08B 24/0461; B64D 11/062; B64D 11/0626; A61B 5/0816; A61B 5/6891; A61M 21/02
USPC ................. 340/573.1, 945, 665–668, 539.12
See application file for complete search history.

(56) References Cited

U.S. PATENT DOCUMENTS 4,831,438 A * 5/1989 Bellman, Jr. .... G08B 13/19634
348/148
5,724,371 A * 3/1998 Magne .................. H01S 3/0675
372/102

(Continued)

*Primary Examiner* — Eric M Blount
(74) *Attorney, Agent, or Firm* — Prakash Nama; Global IP Services, PLLC

(57) ABSTRACT

An aircraft occupant seat for providing health, safety, and comfort management to aircraft occupants is disclosed. In one embodiment, an aircraft occupant, seated in an aircraft occupant seat in an aircraft, is monitored for health, safety and comfort information using at least one sensor disposed in the aircraft occupant seat. Further, background auditory, electrical noise, temperature and mechanical vibration associated with the aircraft occupant seat is measured using the at least one sensor. The health, safety and comfort information associated with the aircraft occupant is then obtained using the monitored health safety and comfort information and the measured background electrical noise and mechanical vibration. Health, safety and comfort of the aircraft occupant are then managed based on the obtained health, safety and comfort information.

18 Claims, 5 Drawing Sheets

(51) Int. Cl.
*B64D 11/06* (2006.01)
*A61B 5/00* (2006.01)
*A61B 5/08* (2006.01)
*A61M 21/02* (2006.01)
*G02B 6/02* (2006.01)
*A61M 21/00* (2006.01)

(56) References Cited

U.S. PATENT DOCUMENTS

| | | | | |
|---|---|---|---|---|
| 6,249,913 | B1* | 6/2001 | Galipeau | H04N 7/17318 |
| | | | | 348/E5.002 |
| 7,183,930 | B2* | 2/2007 | Basir | A61B 5/02455 |
| | | | | 340/521 |
| 7,482,938 | B2* | 1/2009 | Suzuki | B60N 2/002 |
| | | | | 340/425.5 |
| 7,650,803 | B2* | 1/2010 | Ando | A61B 5/103 |
| | | | | 73/862.391 |
| 7,932,837 | B2* | 4/2011 | Giesa | B60R 22/48 |
| | | | | 244/122 R |
| 8,941,499 | B2* | 1/2015 | Fung | A61B 5/6893 |
| | | | | 340/425.5 |
| 9,468,388 | B2* | 10/2016 | Nishii | A61B 5/6891 |
| 9,589,106 | B2* | 3/2017 | Bangera | G06F 19/345 |
| 9,864,842 | B2* | 1/2018 | Hyde | G16H 20/13 |
| 2006/0187015 | A1* | 8/2006 | Canfield | H04B 3/548 |
| | | | | 340/474 |
| 2008/0015753 | A1* | 1/2008 | Wereley | B60N 2/4242 |
| | | | | 701/45 |
| 2008/0103368 | A1* | 5/2008 | Craine | A61B 5/0002 |
| | | | | 600/300 |
| 2010/0036209 | A1* | 2/2010 | Ferren | A61B 5/0002 |
| | | | | 600/301 |
| 2013/0069630 | A1* | 3/2013 | Manson | G01L 9/08 |
| | | | | 324/109 |
| 2013/0070043 | A1* | 3/2013 | Geva | B60K 28/066 |
| | | | | 348/14.02 |
| 2013/0338857 | A1* | 12/2013 | Sampigethaya | A61B 5/6887 |
| | | | | 701/3 |
| 2014/0039330 | A1* | 2/2014 | Seo | A61B 5/0452 |
| | | | | 600/509 |
| 2015/0133804 | A1* | 5/2015 | Sugiyama | A61B 5/0408 |
| | | | | 600/509 |
| 2015/0313475 | A1* | 11/2015 | Benson | A61B 5/6893 |
| | | | | 297/217.3 |
| 2016/0320219 | A1* | 11/2016 | Hellevang | G01F 1/66 |
| 2016/0354027 | A1* | 12/2016 | Benson | A61M 21/02 |

* cited by examiner

AIRCRAFT OCCUPANT SEAT FOR AIRCRAFT OCCUPANT HEALTH, SAFETY, AND COMFORT MANAGEMENT

RELATED APPLICATION

Benefit is claimed under 35 U.S.C. 119(a)-(d) to Foreign Application Serial No. 4790/CHE/2015 filed in India entitled "AIRCRAFT OCCUPANT SEAT FOR AIRCRAFT OCCUPANT HEALTH, SAFETY, AND COMFORT MANAGEMENT", filed on Sep. 9, 2015 by AIRBUS GROUP INDIA PRIVATE LIMITED which is herein incorporated in its entirety by reference for all purposes.

TECHNICAL FIELD

Embodiments of the present subject matter generally relate to vehicle occupant seats, and more particularly, to aircraft occupant seats.

BACKGROUND

Aircraft manufacturers, airlines and other operators of commercial and other aircraft may recognize the desirability of being able to cater to the health, safety and comfort of aircraft occupants. As a result, aircraft may be designed to include various systems and aircraft operators may also provide various services that are intended to support the health, safety and comfort of aircraft occupants.

For example, aircraft may include equipment for monitoring and controlling environmental conditions in an aircraft cabin. In some aircraft, equipment may be provided that allows passengers to adjust environmental conditions at their own seats in the aircraft cabin to some degree. Airlines may also provide various services for supporting the health, safety and comfort of occupants of an aircraft. For example, an airline may provide an in-flight food service, seat/headrest position and temperature control and so on. Many current commercial and other aircraft may include equipment that may allow the occupants of the aircraft to provide an on-demand response to medical emergencies on the aircraft.

However, with the current systems and services, occupant's health, safety and comfort may be hard to evaluate and advance warning of any potential degradation/long term monitoring to prevent incidents is not possible and it may be even harder to provide, a tailored wellbeing to each aircraft occupant as each occupant may respond differently to an aircraft environment based on their health, emotional and physical state, such as whether they are fatigued and/or having medical problems. Further, monitoring and providing, needed comfort to each occupant during flight may pose another challenge.

SUMMARY

An aircraft occupant seat for aircraft occupant health, safety, and comfort management is disclosed. According to one aspect of the present subject matter, an aircraft occupant, seated in an aircraft occupant seat in an aircraft, is monitored for health, safety and comfort information using at least one sensor disposed in the aircraft occupant seat. Further, background electrical noise and mechanical vibration associated with the aircraft occupant seat is measured using the at least one sensor. The health, safety and comfort information associated with the aircraft occupant is then obtained using the monitored health, safety, and comfort information and the measured background electrical noise and mechanical vibration. Health, safety and comfort management of the aircraft occupant are then managed based on the obtained health, safety and comfort information. And alerts can be provided to the crew members to prevent deterioration via early warning, systems/long term health trend monitoring.

According to another aspect of the present subject matter, the aircraft occupant seat may include an aircraft occupant health, safety and comfort management system. Further, the aircraft occupant health, safety and comfort management system may include at least one processor, a network interface card to couple to an aircraft network data processing system residing in an aircraft, at least one sensor disposed in the aircraft occupant seat, and a storage device coupled to the at least one processor. Furthermore, the storage device may include an aircraft occupant health, safety and comfort management module (AOHSCMM) to perform the method described above.

The system and method disclosed herein may be implemented in any means for achieving various aspects. Other features will be apparent from the accompanying drawings and from the detailed description that follow.

BRIEF DESCRIPTION OF THE DRAWINGS

Various embodiments are described herein with reference to the drawings, wherein.

The drawings described herein are for illustration purposes only and are not intended to limit the scope of the present disclosure in any way.

DETAILED DESCRIPTION

A system and method for providing aircraft occupant health, safety and comfort management via aircraft occupant seat are disclosed. In the following detailed description of the embodiments of the present subject matter, references are made to the accompanying drawings that form a part hereof, and in which are shown by way of illustration specific embodiments in which the present subject matter may be practiced. These embodiments are described in sufficient detail to enable those skilled in the art to practice the present subject matter, and it is to be understood that other embodiments may be utilized and that chances may be made without departing from the scope of the present subject matter. The following detailed description is, therefore, not to be taken in a limiting sense, and the scope of the present subject matter is defined by the appended claims.

Embodiments described herein provide systems and methods for aircraft occupant health, safety, comfort management and long term monitoring via an aircraft occupant seat. The example technique disclosed herein significantly reduces manpower for providing aircraft occupant health, safety and comfort. Further the systems and methods described herein may reduce unnecessary diversions and may direct the flight to a nearest available facility for providing aircraft occupant health, safety and comfort or facilitate remote assistance. Furthermore, the systems and methods may utilize best available medical practices when a physician is not on board the aircraft. In addition, the systems and methods may significantly reduce chances of losing the aircraft when a pilot is medically incapacitated or long term monitoring trends may suggest that a medical emergency may be imminent. Also, the systems and methods may facilitate in recognizing a situation & transferring the control of the aircraft to another pilot or ground station in case the pilot is incapacitated. Moreover, the systems and methods may send alerts in case of non-compliance of aircraft occupant health, safety, security and comfort.

Figure 1:
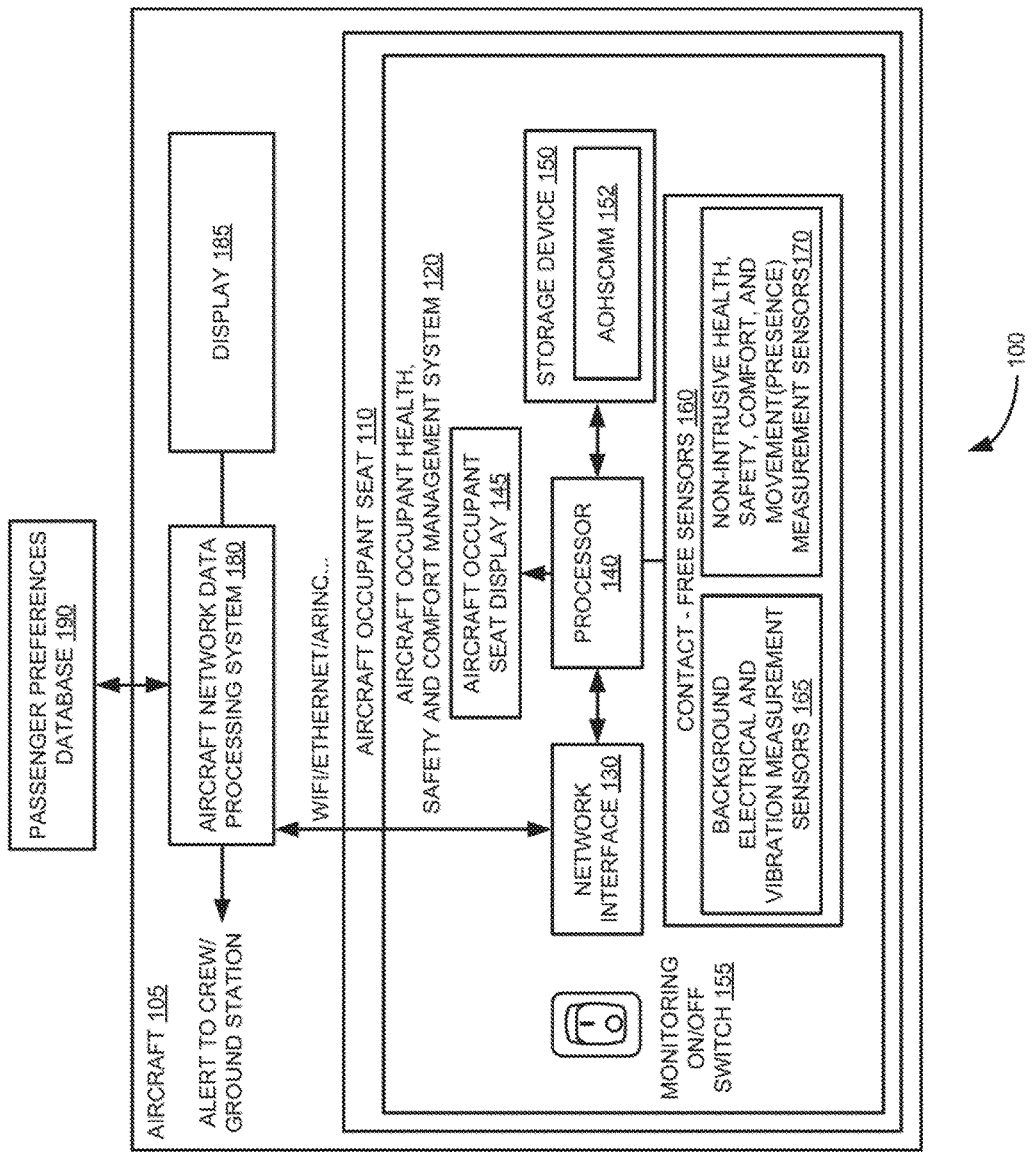
FIG. 1 is a block diagram illustrating a system for managing aircraft occupant health, safety and comfort via an aircraft occupant seat, according to an embodiment.

Referring now to FIG. 1, which is a block diagram 100 illustrating an exemplary aircraft occupant seat 110 including an aircraft occupant health, safety and comfort management system 120 for managing health, safety and comfort of an aircraft occupant seated in the aircraft occupant seat 110 in an aircraft 105. The term "aircraft occupant" refers to anyone seated in the aircraft, such as pilot, passenger, cabin-crew and the like. As shown in FIG. 1, the aircraft occupant health safety and comfort management system 120 includes a network interface 130 to couple to an aircraft network data processing system 180 disposed in the aircraft 105. Further as shown in FIG. 1, the aircraft occupant health safety and comfort management system 120 includes a processor 140 coupled to the network interface 130, a storage device 150 coupled to the processor 140, contact-free sensors 160 coupled to the processor 140, and a display 145 coupled to the processor 140. Also as shown in FIG. 1, contact-free sensors 160 include background electrical noise and vibration measurement sensors 165 and non-intrusive health, safety, comfort, and movement measurement sensors 170.

In addition, the aircraft occupant health, safety and comfort management system 120 includes a monitoring on/off switch 155, which may be used by an aircraft occupant to turn on and off the aircraft occupant health safety and comfort management system 120. Further, the monitoring on/off switch 155 may be configured to turn on/off personal information associated with the aircraft occupant and not the information associated with security and safety. For example, not providing ability to the aircraft occupant for switching off the alerts on removal of lifejacket and/or oxygen mask or seatbelt from the aircraft occupant seat 110.

In addition as shown in FIG. 1, the network interface 130 is communicatively coupled to the aircraft network data processing, system 180 via WIFI, ETHERNET, ARINC, and the like. Moreover as shown in FIG. 1, the aircraft 105 includes a display 185 coupled to the aircraft network data processing system 180. Furthermore as shown in FIG. 1, passenger preferences database 190 is coupled to the aircraft network data processing system 180.

Figure 3:
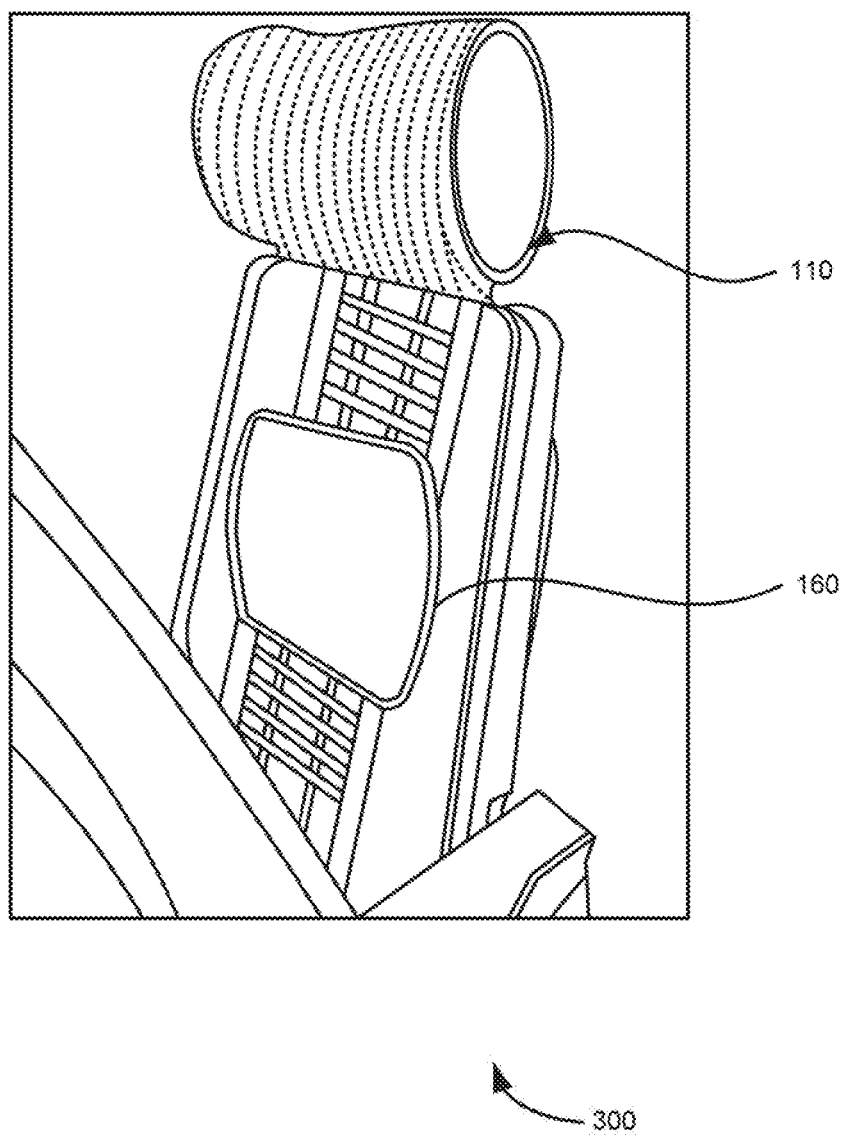
FIGS. 3 and 4 are schematic diagrams showing example dispositions of the contract-free piezo-electric sensors in an aircraft occupant seat for aircraft occupant health, safety and comfort management, according to an embodiment.
Figure 4:
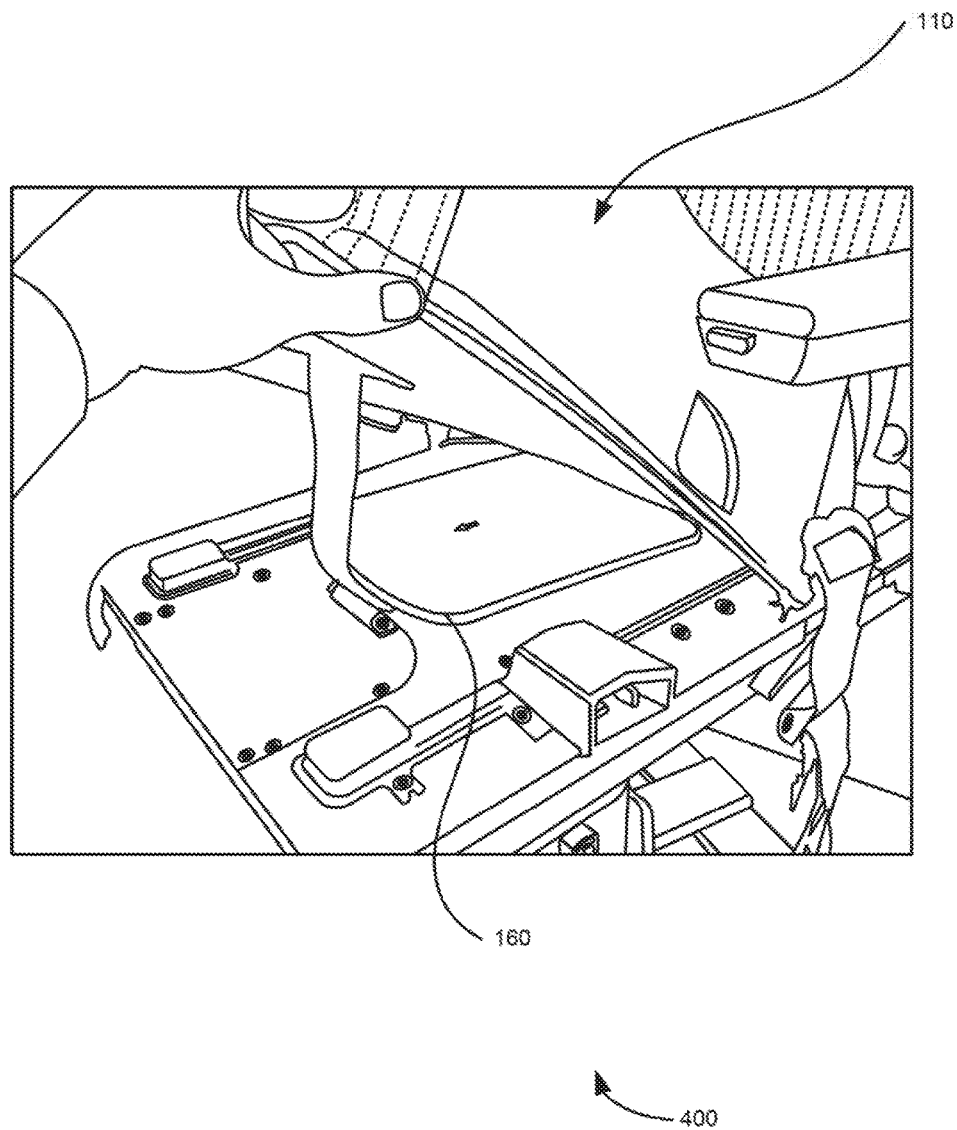
Figure 5:
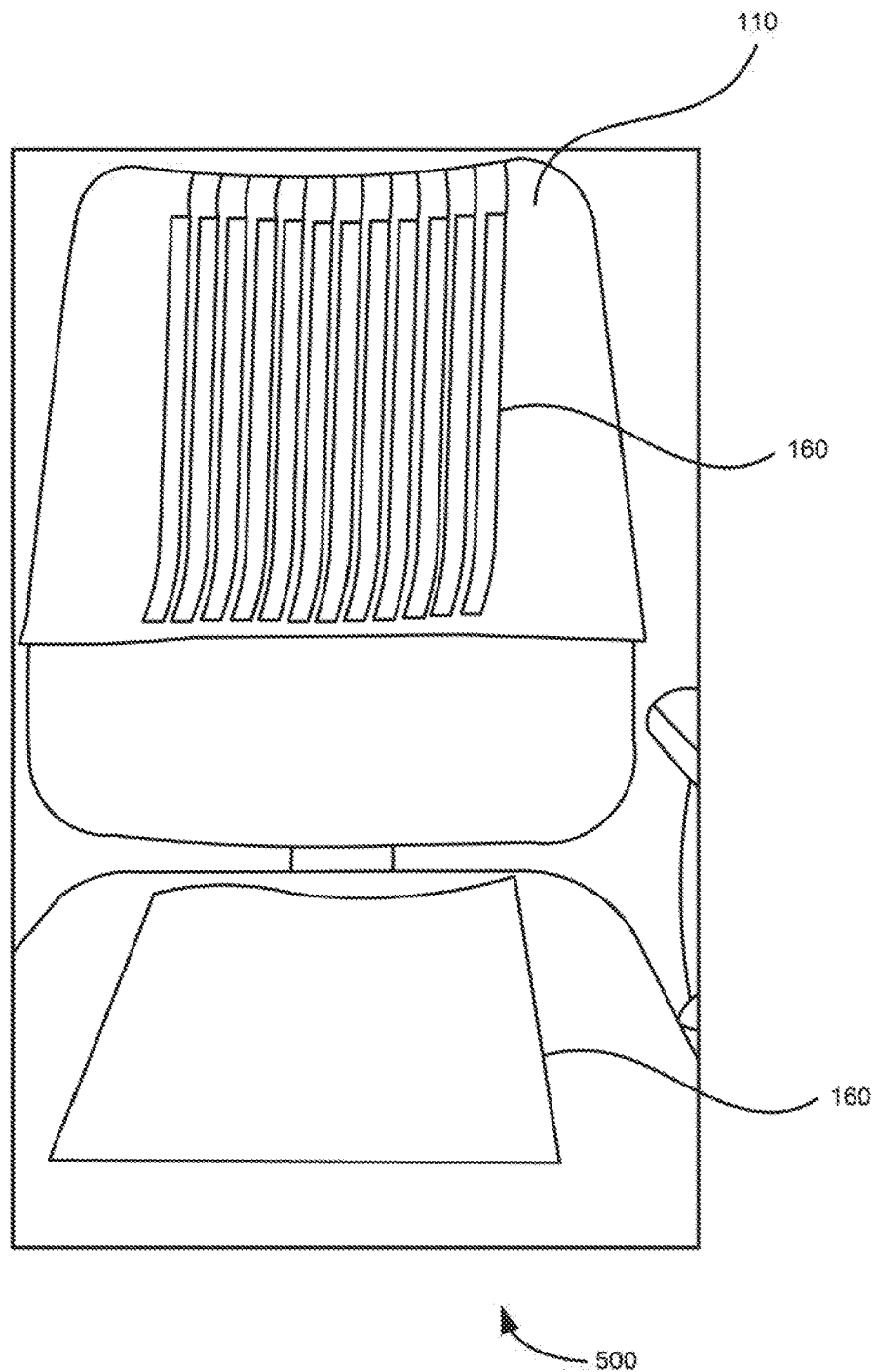
FIG. 5 is a schematic diagram showing example disposition of electro-potential EKG and ECG sensors (i.e., fabric embedded electrode wires) in the aircraft occupant seat cover on the seatback or headrest for aircraft occupant health, safety and comfort management, according to an embodiment.

In operation, aircraft occupant health, safety and comfort management module (AOHSCMM) 152 monitors an aircraft occupant, seated in the aircraft occupant seat 110 in the aircraft 105, for health, safety and comfort information using at least one sensor 160 disposed in the aircraft occupant seat 110. Example at least one sensor is a contact-free sensor and/or a non-intrusive sensor. Further example, at least one sensor is a piezoelectric sensor, electrometer (electric potential measurement sensor), and/or optical fiber bragg grating optical sensor. FIGS. 3 and 4 show a contact-free sensor 160 disposed in the aircraft occupant seat 110. It can be seen that the contact-free sensor 160 may be disposed in the aircraft occupant seat 110 to accommodate varying sizes and positions of the aircraft occupant. In the example shown in FIGS. 3 and 4, the piezoelectric sensor is disposed below or behind the seat cushion of the aircraft occupant seat 110. Further in the example shown in FIG. 5, the electro-potential sensors are disposed on the surface and/or integrated as part of the aircraft occupant seat cover. One can envision, that the electro-potential sensors can be disposed in the aircraft occupant seat headrest to measure alpha/beta brain wake to check sleep level (i.e., rapid eye movement (REM)/Non REM sleep). For example, REM may occur when a person is dreaming, and in such a scenario coordinating the blue/green light at the end of REM phase may be very effective to the aircraft occupant.

In one example embodiment, the non-intrusive health, safety, comfort, and movement sensor 170 is used for measuring vital signs of the aircraft occupant. Further in example embodiment, non-intrusive health, safety, comfort, and movement sensor 170 is used for measuring chest muscle movement (i.e., for measuring breathing rate), sense pulse via ballistocardiogram (BCG), and wakefulness/sleep level, of the aircraft occupant. For example, the non-intrusive health, safety, comfort, and movement sensor 470 disposed in the bottom of the aircraft occupant seat may be configured to sense heart rate and breathing rate by body recoil (i.e., ballistogcardiagram) without having to measure chest wall movement. For example, measuring total body movement and then filtering the combined frequency signal into heat and breathing rates.

Further in operation, the AOHSCMM 152 measures background electrical noise and mechanical vibration associated with the aircraft occupant seat 110 using the at least one sensor 160. Furthermore in operation, the AOHCMM 152 obtains the health, safety and comfort information associated with the aircraft occupant using the monitored health safety and comfort information and the measured background electrical noise and mechanical vibration.

In addition in operation, the AOHCMM 152 manages health, safety and comfort of the aircraft occupant based on the obtained health, safety and comfort information. Example health, safety and comfort management of the aircraft occupant includes adjusting airflow vent/air conditioner temperature substantially around the occupant seat based, providing ability to obtain waiting position number for the washroom and informing the aircraft occupant about availability of washroom upon reaching the obtained waiting position number, notifying seat belt condition to the aircraft cabin crew, providing blue/green light to awake the aircraft occupant, providing an optimized seating position to the aircraft occupant, providing seat presence or absence signal to cabin crew, providing appropriate audio level to the aircraft occupant, providing ambient noise cancellation or white noise to the occupant, providing appropriate refreshments to the aircraft occupant, providing emergency equipment condition information to the cabin crew, and/or providing condition of personal electronic equipment connected to the aircraft occupant based on the obtained health, safety and comfort information.

Also in operation, the AOHCMM 152 may send an alert to crew/ground station or display the health, safety and comfort information on the displays 145 and/or 185 via the aircraft network data processing system 180 based on the obtained health, safety and comfort information. Further in operation, one can envision configuring AOHCMM 152 to provide the ability to warn about removal of flight safety equipment from aircraft occupant seat 110 to cabin crew (For example, removal of oxygen mask or life jacket) so cabin-crew can prevent removal at disembarkation). Furthermore in operation, configuring AOHCMM 152 to provide ability to decide where to route the alerts during different flight phases. For example, if a passenger is ill before takeoff, both the pilot and the cabin crew may be alerted. Further for example, if during takeoff and/or landing only cabin crew may be alerted. Also for example, during flight displaying the seat belt or tray table alert/reminder to occupant or cabin crew when not complied.

Figure 2:
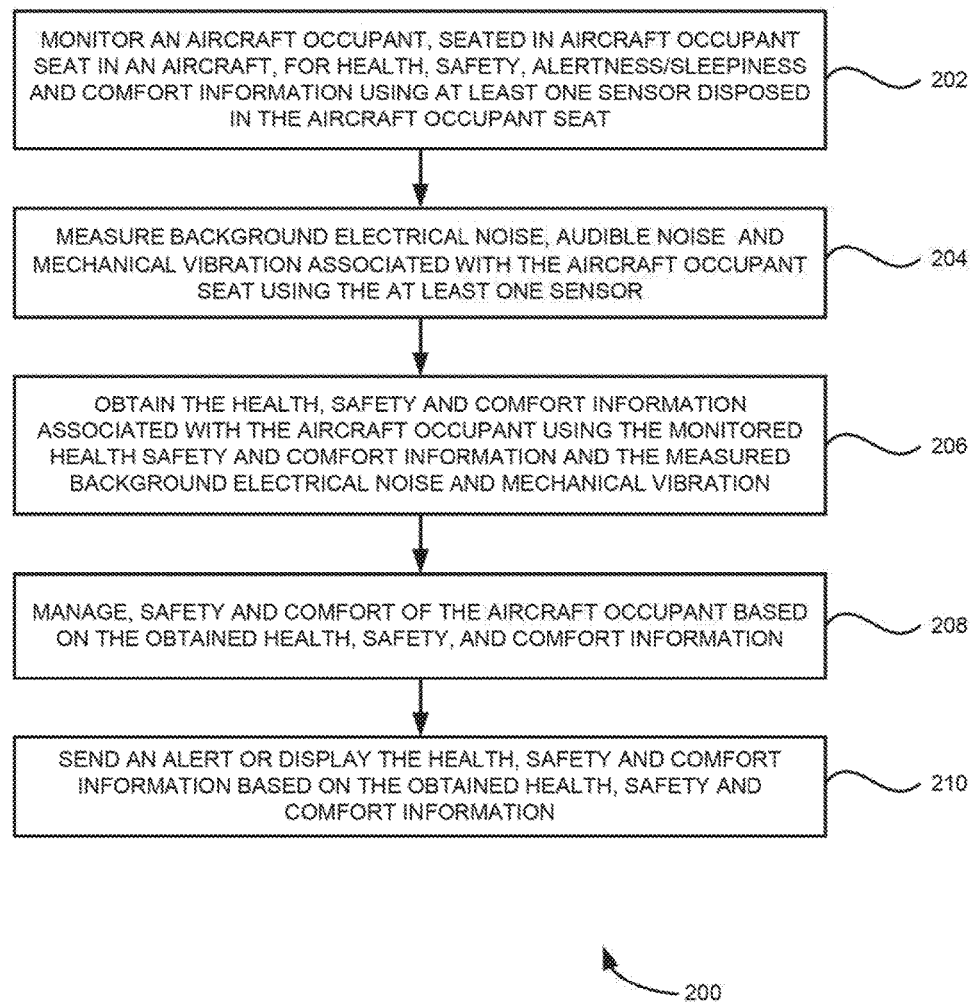
FIG. 2 is a flowchart illustrating a process for aircraft occupant health, safety and comfort management via an aircraft occupant seat, according to an embodiment.

Referring now to FIG. 2, which illustrates a flow diagram 200 of an exemplary method for aircraft occupant health, safety and comfort management. At block 202, an aircraft occupant, seated in an aircraft occupant seat in an aircraft, is monitored for health, safety, alertness/sleepiness, and comfort information using at least one sensor disposed in the aircraft occupant seat. At block 204, background electrical noise, audible noise, and/or mechanical vibration associated with the aircraft occupant seat is measured using the at least one sensor. At block 206, the health, safety and/or comfort information associated with the aircraft occupant is obtained using the monitored health safety and comfort information and the measured background electrical noise and mechanical vibration. At block 208, health, safety and comfort of the aircraft occupant is managed based on the obtained health, safety and comfort information. At block 210, an alert is sent to crew/ground station or displaying the health, safety and comfort information on a display device based on the obtained health, safety and comfort information. This method is explained in more detail with reference to FIG. 1 and FIGS. 3-5.

Although the present embodiments have been described with reference to specific example embodiments, it will be evident that various modifications and changes may be made to these embodiments without departing from the broader spirit and scope of the various embodiments. Furthermore, the various devices, modules, analyzers, generators, and the like described herein may be enabled and operated using hardware circuitry, for example, complementary metal oxide semiconductor based logic circuitry, firmware, software and/or any combination of hardware, firmware, and/or software embodied in a machine readable medium. For example, the various electrical structure and methods may be embodied using transistors, logic gates, and electrical circuits, such as application specific integrated circuit.

What is claimed is:

1. A method, for aircraft occupant health, safety and comfort management via an aircraft occupant seat, comprising:
    monitoring an aircraft occupant, seated in an aircraft occupant seat in an aircraft, for health, safety, alertness/sleepiness, and comfort information using at least one sensor disposed in the aircraft occupant seat;
    measuring background electrical noise, audible noise, and mechanical vibration associated with the aircraft occupant seat using the at least one sensor;
    obtaining the health, safety and comfort information associated with the aircraft occupant using the monitored health, safety and comfort information and the measured background electrical noise and mechanical vibration; and
    managing health, safety and comfort of the aircraft occupant based on the obtained health, safety and comfort information, wherein managing the health, safety and comfort of the aircraft occupant comprises adjusting airflow vent/air conditioner temperature substantially around the aircraft occupant seat.

2. The method of claim 1, further comprising:
    sending an alert to crew/ground station or displaying the health, safety and comfort information on a display device based on the obtained health, safety and comfort information.

3. The method of claim 1, wherein the at least one sensor is a contact-free/air gap sensor.

4. The method of claim 3, wherein the at least one sensor is selected from the group consisting of piezoelectric sensor, electric potential measurement sensor, and optical fiber bragg grating sensor.

5. The method of claim 1, wherein the at least one sensor is disposed in the aircraft occupant seat or headrest to accommodate varying sizes and positions of the aircraft occupant.

6. The method of claim 1, wherein the at least one sensor is used for measuring vital signs of the aircraft occupant.

7. The method of claim 1, wherein the at least one sensor is used for measuring chest muscle movement/breathing rate of the aircraft occupant.

8. The method of claim 1, wherein management of the health, safety and comfort to the aircraft occupant comprises providing ability to obtain waiting position number for washroom and informing the aircraft occupant about availability of the washroom upon reaching the obtained waiting position number, notifying seat belt condition to the aircraft occupant, providing a timed/scheduled blue/green light to the aircraft occupant based on directed light to nerve receptors behind eyes/temple or ears to help aircraft occupant wakeup gradually, providing an optimized seating position to the aircraft occupant, providing appropriate audio level to the aircraft occupant, providing appropriate refreshments to the aircraft occupant, providing seat presence or absence signal to cabin crew, providing ambient noise cancellation or white noise to the aircraft occupant, providing emergency equipment condition information to the cabin-crew, and/or providing condition of personal electronic equipment connected to the aircraft occupant based on the obtained health, safety, background electrical noise and comfort information.

9. The method of claim 1, further comprising:
    providing ability to turn-on and turn-off the monitoring of the health, safety and comfort information by the aircraft occupant.

10. An aircraft occupant seat, comprising:
    an aircraft occupant health, safety and comfort management system, wherein the aircraft occupant health, safety and comfort management system, comprises:
    at least one processor;
    a network interface card to couple to an aircraft network data processing system residing in an aircraft;
    at least one sensor disposed in the aircraft occupant seat; and
    memory coupled to the at least one processor, wherein the memory comprises an aircraft occupant health, safety and comfort management module (AOHCMM) to:
        monitor an aircraft occupant, seated in an aircraft occupant seat in an aircraft, for health, safety, alertness/sleepiness and comfort information using the at least one sensor disposed in the aircraft occupant seat;
        measure background electrical noise, audible noise and mechanical vibration associated with the aircraft occupant seat using the at least one sensor;

obtain the health, safety and comfort information associated with the aircraft occupant using the monitored health, safety and comfort information and the measured background electrical noise and mechanical vibration; and provide health, safety and comfort management to the aircraft occupant based on the obtained health, safety and comfort information, wherein providing the health, safety and comfort management to the aircraft occupant comprises adjusting airflow vent/air conditioner temperature substantially around the occupant seat.

11. The aircraft, occupant seat of claim 10, wherein the AOHCMM sends an alert to crew/ground station or displaying the health, safety and comfort information on a display device based on the obtained health, safety and comfort information.

12. The aircraft occupant seat of claim 10, wherein the at least one sensor is a contact-free sensor.

13. The aircraft occupant seat of claim 12, wherein the at least one sensor is selected from the group consisting of piezoelectric sensor, electric potential measurement sensor, and optical fiber or brag grating sensor.

14. The aircraft occupant seat of claim 10, wherein the at least one sensor is disposed in the aircraft occupant seat to accommodate varying sizes and positions of the aircraft occupant.

15. The aircraft occupant seat of claim 10, wherein the at least one sensor is used for measuring vital signs of the aircraft occupant.

16. The aircraft occupant seat of claim 10, wherein the at least one sensor is used for measuring chest muscle movement, sense pulse via ballistocardiogram (BCG) of the aircraft occupant.

17. The aircraft occupant seat of claim 10, wherein management of the health, safety and comfort to the aircraft occupant comprises providing ability to obtain waiting position number for washroom and informing the aircraft occupant about availability of the washroom upon reaching the obtained waiting position number, notifying seat belt condition to the aircraft occupant, providing a timed/scheduled blue/green light to the aircraft occupant to help aircraft occupant wakeup gradually, providing an optimized seating position to the aircraft occupant, providing appropriate audio level to the aircraft occupant, providing appropriate refreshments to the aircraft occupant, providing seat presence or absence signal to cabin-crew, providing ambient noise, cancellation or white noise to the aircraft occupant, providing emergency equipment condition information to the cabin-crew, and/or providing condition of personal electronic equipment connected to the aircraft occupant based on the obtained health, safety, background electrical noise and comfort information.

18. The aircraft occupant seat of claim 10, wherein the AOHCMM is configured to turn-on and turn-off the monitoring of the health, safety and comfort information by the aircraft occupant.

* * * * *